US00PP10959P

United States Patent [19]

Bull

[11] Patent Number: Plant 10,959

[45] Date of Patent: Jun. 15, 1999

[54] NEW GUINEA IMPATIENS PLANT NAMED 'FLORA'

[76] Inventor: Norbert Bull, Gaertnersiedlung 2, 24610 Goennebek, Germany

[21] Appl. No.: 08/897,984

[22] Filed: Jun. 23, 1997

[51] Int. Cl.[6] ..... A01H 5/00

[52] U.S. Cl. ..... Plt./87.6

[58] Field of Search ..... Plt./87.6

[56] References Cited

U.S. PATENT DOCUMENTS

P.P. 8,360 8/1993 Bull ..... Plt./87.6

OTHER PUBLICATIONS

GTITM Upovrom Citation for 'Flora' as Per NL PBR BLM0196, Jul. 16, 1994.

GTITM Upovrom Citation for 'Flora' as Per DE PBR 00296, Jun. 15, 1994.

*Primary Examiner*—Howard J. Locker
*Assistant Examiner*—Kent L. Bell
*Attorney, Agent, or Firm*—Foley & Lardner

[57] ABSTRACT

A new and distinct cultivar of New Guinea Impatiens plant named 'Flora', characterized by its salmon red flower color with white eye having pink-violet center, medium to large, round flowers, intense green foliage with no variegation, compact plant habit, and early flowering response.

1 Drawing Sheet

The present invention comprises a new and distinct cultivar of New Guinea Impatiens, referred to by the cultivar name 'Flora'.

'Flora' is a product of a planned breeding program and was originated from a hybridization made by the inventor Norbert Bull in a controlled breeding program in Goennebek, Germany, in 1992. The female parent was a seedling designated No. 2 and the male parent was a seedling designated No. 4. Both parents are proprietary cultivars used in the breeding program.

'Flora' was discovered and selected as one flowering plant within the progeny of the stated cross by the inventor in 1992 in a controlled environment in Goennebek, Germany.

The first act of vegetative or asexual reproduction of 'Flora' was accomplished when cuttings were taken from the initial selection in winter 1992/93 in a controlled environment in Goennebek, by, or under the supervision of, Norbert Bull.

Horticultural examination of plants grown from cuttings of the clone initiated in Spring 1993 in Goennebek, Germany, and continuing thereafter, has demonstrated that the combination of characteristics as herein disclosed for 'Flora' are firmly fixed and are retained through successive generations of asexual reproduction.

'Flora' has not been observed under all possible environmental conditions. The phenotype may vary significantly with variations in environment such as temperature, light intensity and day length, without, however, any variation in genotype.

The following observations, measurements, and comparisons describe plants grown in Hillscheid, Federal Republic of Germany under greenhouse conditions which approximate those generally used in commercial practice.

The following traits have been repeatedly observed and are determined to be basic characteristics of 'Flora' which in combination distinguish this impatiens as a new and distinct cultivar:

1. Salmon red flower color with a white eye.
2. Medium to large, round flowers.
3. Intense green foliage.
4. Compact plant habit.
5. Early flowering response.
6. Resistant to powdery mildew.

Of the many commercial cultivars known to the present inventor, the most similar in comparison to 'Flora' is the cultivar 'Celebration Salmon' (U.S. Plant Pat. No. 8,870). In comparison to 'Celebration Salmon', the flower color of 'Flora' has a slightly different salmon hue, and plants of 'Flora' start flowering somewhat earlier. Further, in contrast to the uniform green colored foliage of 'Flora', leaves of 'Celebration Salmon' are slightly variegated with narrow yellow stripes along the midrib.

The accompanying photographic drawing shows typical flower and foliage characteristics of 'Flora' with colors being as true as possible with illustrations of this type. In this regard, the illustration my not depict the color designations and descriptions as they accurately appear in the botanical description.

In the following description color references are made to The Royal Horticultural Society Color Chart.

The color values were determined indoors from flowers taken from plants grown in Hillscheid, Federal Republic of Germany, under greenhouse conditions which approximate those generally used in commercial practice.

The description is based on plants which were planted as rooted cuttings in 10 cm pots and grown at 20° C. minimum temperature.

Classification:

*Botanical.*—A hybrid of the genus Impatiens.

*Commercial.*—New Guinea Impatiens cv. 'Flora'.

I. PLANT

A. General appearance and form:

*Habit.*—Compact, uniformly molded, round, well branched, and growth is indeterminate, although weak after flowering begins.

*Height.*—11 cm (10-week-old plants).

*Width.*—26 cm.

*Internode length.*—20–30 mm.

*Stem color.*—Reddish to brownish pink.

*Flowering response.*—6–7 weeks after planting of rooted cuttings.

*Flowering season.*—Generally indeterminate, mainly from March to October, depending on light intensity.

*Propagation.*—Usually terminal tips for cuttings.

*Rooting.*—Color is R.H.S. 159 B-C; roots initiate in about 18 days at 22° C., from sticking to transplanting.

B. Foliage:

*Leaf arrangement.*—Primarily in whorls.

*Shape of leaf.*—Elliptic, with acute base and acuminate tip.

*Margin.*—Slightly serrated, ciliated.

*Leaf, length.*—About 115 mm.

*Leaf, width.13* About 32–35 mm.

*Main color of upper surface.*—Medium green, approximately R.H.S. 137B.

*Veins on upper surface, color.*—dark pink to light red, about R.H.S. 47 B, at the very base, but fading significantly toward the tip of the leaf.

*Variegation on leaf.*—Absent.

*Main color of lower surface.*—Light green, about R.H.S. 138B.

*Veins on lower surface, color.*—Medium red.

*Petiole, color.*—Light red, R.H.S. 47 A-B.

*Petiole, length.*—About 10 mm.

*Flower number per node.*—About 6, in various stages of development.

II. INFLORESCENCE

A. Flower:

*Form of corolla.*—Single.

*Shape.*—Nearly round.

*Average diameter.*—6.3 cm.

*Color (general tonality from a distance of three meters)* .—Salmon red.

*Petal number.*—Five (5).

*Petal shape.*—Cordate (heart-shaped), moderately lobed, most often flat, upper petal may be slightly cupped in young plant.

*Petal length.*—30 mm.

*Petal width.*—Upper and lower petals are about 32–35 mm and side petals are about 25 mm.

*Petal texture.*—Smooth, slightly glossy.

*Petal aspect.*—Borne well above the foliage.

*Main color of upper surface.*—Closest to R.H.S. 43A.

*Color of lower surface.*—R.H.S. 43C.

*Eye zone.*—Medium sized, whitish R.H.S. 56D, which suffuses from the eye into the central portion of the petals, with center of eye being pink-violet.

*Spur, color.*—Dark red, R.H.S. 53B.

*Spur shape and size.*—Downwardly curved, about 50–55 mm in length.

*Pedicel, length.*—About 45 mm.

*Pedicel, color.*—Brownish pink, R.H.S. 179B.

III. REPRODUCTIVE ORGANS

*Androecium.*—Stamens: five (5) in number, fused, upper surface color is mainly R.H.S. 43B. Anthers: hooded, color is about R.H.S. 11D. Pollen: color is about R.H.S. 4D.

*Gynoecium.*—Stigma and style: five (5) in number, very short, color is about RHS 11D. Ovary: five (5) celled, about 5 mm in length, surface color is R.H.S. 137B, which may darken as plant matures.

I claim:

1. A new and distinct cultivar of New Guinea Impatiens plant named 'Flora', as illustrated and described.

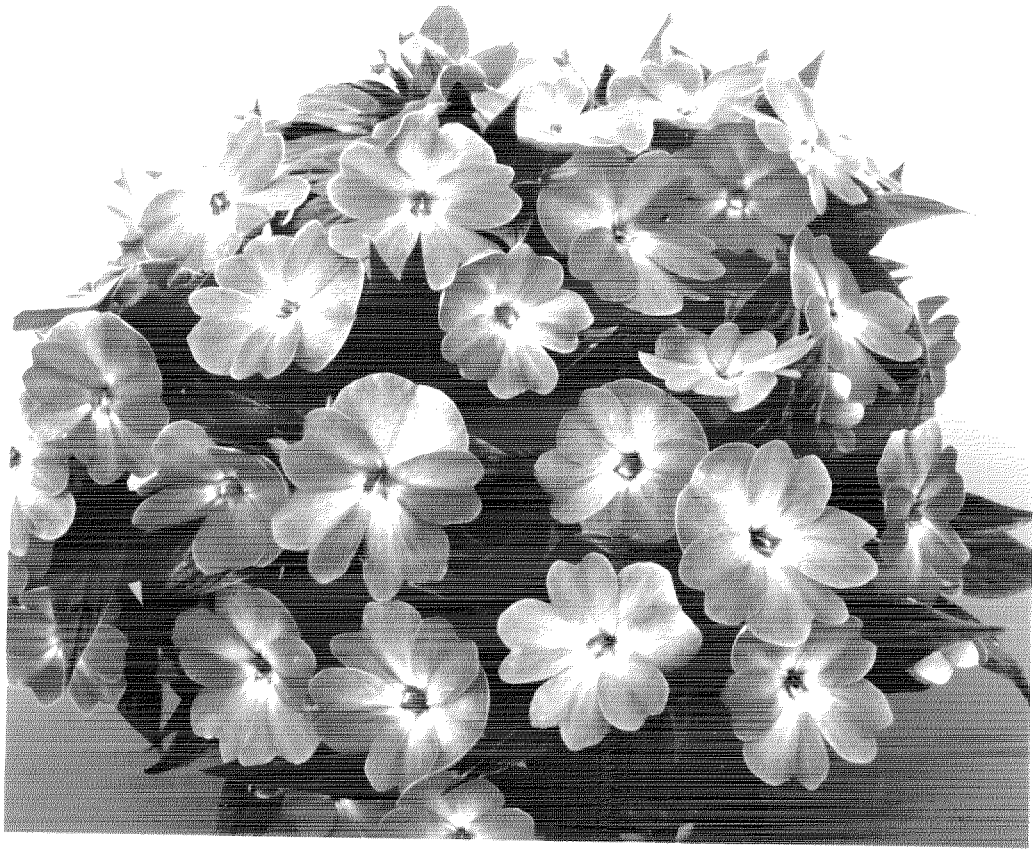

* * * * *